United States Patent [19]

Babin et al.

[11] Patent Number: 5,312,964

[45] Date of Patent: May 17, 1994

[54] NOVEL PROCESS AND INTERMEDIATES

[75] Inventors: Didier Babin, Montigny; Neerja Bhatnagar, Savigny-Sur-Orge; Francis Brion, Gagny; Colette Colladant, Rosny Sous Bois, all of France

[73] Assignee: Roussel UCLAF, France

[21] Appl. No.: 68,251

[22] Filed: May 27, 1993

[30] Foreign Application Priority Data

Jun. 4, 1992 [FR]   France ................. 92 06772

[51] Int. Cl.$^5$ .......................................... C07C 121/75
[52] U.S. Cl. .................................................. 560/124
[58] Field of Search ........................ 560/124; 562/506

[56] References Cited

U.S. PATENT DOCUMENTS

| | | | |
|---|---|---|---|
| 5,004,822 | 4/1991 | Elliott et al. | 560/124 X |
| 5,026,862 | 6/1991 | Tessier et al. | 560/124 |
| 5,030,655 | 7/1991 | Tessier et al. | 560/124 X |
| 5,049,585 | 9/1991 | Robson et al. | 560/124 X |
| 5,245,073 | 9/1993 | Cadiergue et al. | 560/124 |

FOREIGN PATENT DOCUMENTS 2480748  4/1980  France .
2102408  7/1981  United Kingdom .

OTHER PUBLICATIONS

Rapport De Recherche Search Report No. 9206772 & 472332 Chemical Abstracts vol. 95, 1981 p. 488, Chemical Abstracts vol. 103, 1985 p. 596.
Synthetic Communications, 14(13), 1239–1246 (1984).
Organic Synthesis vol. 53 (1973) pp. 123–127.
Journal of Synthetic Organic Chemistry No. 11 Nov. (1989) pp. 785–880.
Tetrahedron Letters, vol. 27, No. 35 pp. 4119–4120, (1986).
Stereoselective preparation of methyl (Z)–Cinnamates by Favorskii rearrangement Engler et al.
International Journal of Methods in Synthetic Organic Chemistry (1984) No. 5 May pp. 428–429–A New Approach to the Synthesis of Methyl (1,S)–cis-3-(-2-Acetoxyalkyl/2-Hydroxyalkyl/2-Oxoalkyl)-2,-2-dimethylcyclopropanecarboxylates from (+)-3-Carene, Mitra, et al.

*Primary Examiner*—Arthur C. Prescott
*Attorney, Agent, or Firm*—Bierman and Muserlian

[57] ABSTRACT

A novel process for the preparation of isomers or mixtures of isomers of compounds of the formula

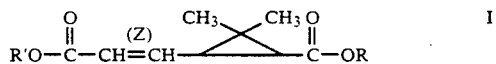

and novel intermediates therefore.

15 Claims, No Drawings

NOVEL PROCESS AND INTERMEDIATES

OBJECTS OF THE INVENTION

It is an object of the invention to provide an improved process for the preparation of compounds of formula I and novel intermediates formed therein.

This and other objects and advantages of the invention will become obvious from the following detailed description.

THE INVENTION

The novel process of the invention for the preparation of a compound of the formula

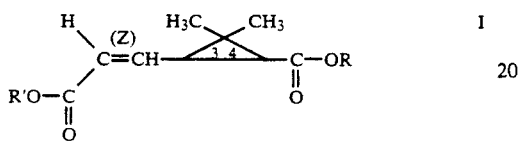

wherein R is either a remainder of a cleavable ester or a remainder of an ester known for pyrethrinoids selected from the group consisting of:

a) benzyl optionally substituted on the aromatic vertices by at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogen;

b)

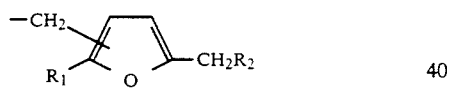

in which $R_1$ is hydrogen or methyl and $R_2$ is a monocyclic aryl or —C≡CH;

c)

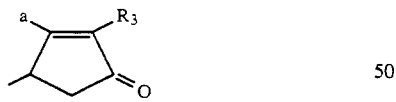

in which a hydrogen or methyl and $R_3$ is aliphatic of 2 to 6 carbon atoms and having at least one carbon-carbon unsaturation;

d)

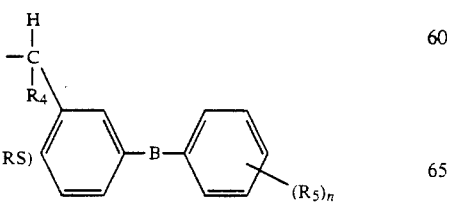

in which B is oxygen or sulfur or

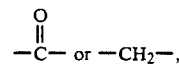

$R_4$ is selected from the group consisting of hydrogen, chlorine, bromine, iodine, —C≡N, methyl, —CONH$_2$, —CSNH$_2$ and —C≡CH, $R_5$ is halogen or methyl and n is 0, 1 or 2;

e)

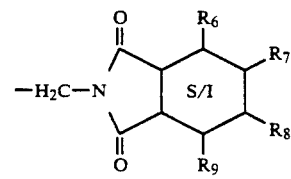

in which $R_6$, $R_7$, $R_8$ and $R_9$ are hydrogen, chlorine or methyl and in which S/I symbolizes an aromatic ring or a dihydro, tetrahydro or hexahydro ring;

f) (succimido or maleimido) methylene;

g)

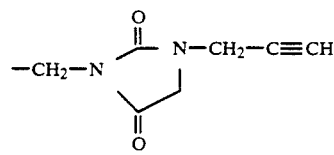

h)

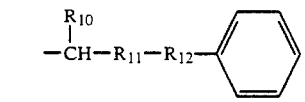

in which $R_{10}$ is hydrogen or CN, $R_{12}$ is —CH$_2$ or oxygen, $R_{11}$ is thiazolyl or thiadiazolyl whose bond with

can be found in any one of the available positions, $R_{12}$ being linked to $R_{11}$ by the carbon atom contained between the sulfur and the nitrogen;

i)

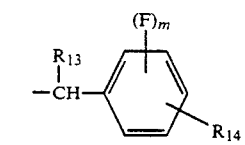

in which $R_{13}$ is hydrogen or —CN or —C≡CH, $R_{14}$ is trifluoromethyl or alkyl, alkenyl or alkynyl of up to 6 carbon atoms and m is a number of 1, 2, 3 or 4;

j)

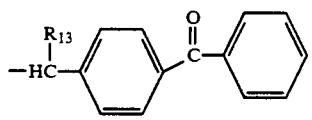

in which R₁₃ is defined as above;

k)

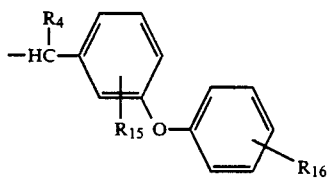

in which R₄ is defined as above, R₁₅ is fluorine, chlorine or bromine and R₁₆ is hydrogen, fluorine, chlorine or bromine;

l)

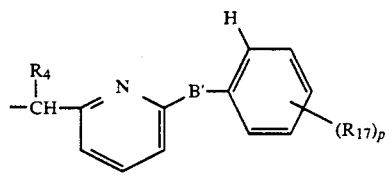

in which R₄ is defined as above, each of R₁₇ is independently selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo, p is 0, 1 or 2 and B' is oxygen or sulfur;

m)

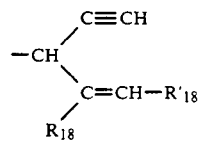

in which R₁₈ is fluorine or methyl and R'₁₈ is methyl, ethyl or propargyl;

n)

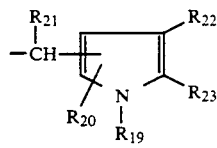

in which R₂₁ is hydrogen —C≡N, —C≡CH, —CF₃ or alkyl of 1 to 3 carbon atoms, R₂₀, R₂₂ and R₂₃ individually are selected from the group consisting of hydrogen, halogen, alkyl of 1 to 18 carbon atoms, aryl of up to 14 carbon atoms, aralkyl of up to 18 carbon atoms, cyano, —CF₃, —CO₂-alkyl of up to 8 carbon atoms, NO₂, alkoxy of up to 8 carbon atoms,

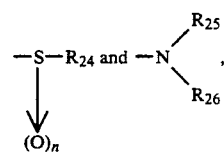

n is 0, 1 and 2 and R₂₄, R₂₅ and R₂₆ are alkyl of 1 to 8 carbon atoms, R₂₂ and R₂₃ being able to form a saturated or unsaturated carbonaceous homocycle of up to 8 carbon atoms and R₁₉ is:
a) either

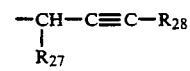

in which R₂₇ and R₂₈ are individually hydrogen, halogen, alkyl of 1 to 8 carbon atoms or aryl of up to 14 carbon atoms;

b) or

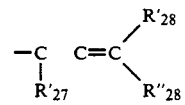

in which R'₂₇, R'₂₈ and R''₂₈ are individually one of the values for R₂₇ and R₂₈, the dotted lines being an optional second bond;

c) or

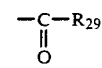

in which R₂₉ can have the values indicated for R₂₂ and R₂₃ with the exception of halogen, cyano, —NO₂,

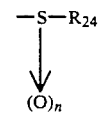

in which n is 1 or 2 and

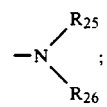

d) or

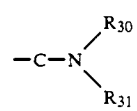

in which R₃₀ and R₃₁ are individually hydrogen, alkyl of 1 to 18 carbon atoms, aryl of up to 14 carbon atoms, aralkyl of up to 18 carbon atoms, —CF₃, —CO₂-alkyl of up to 8 carbon atoms or alkoxy of up to 8 carbon atoms.

o)

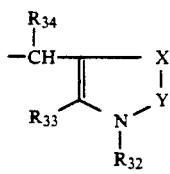

in which X is sulfur or oxygen, Y is >C=O, >C=S or —CH₂, R₃₂ is selected from the group consisting of saturated or unsaturated, alkyl or cycloalkyl of up to 8 carbon atoms optionally substituted by at least one halogen and aryl of up to 14 carbon atoms, R₃₃ is selected from the group consisting of hydrogen, saturated or unsaturated alkyl or cycloalkyl of up to 8 carbon atoms optionally substituted by at least one halogen, aryl of up to 14 carbon atoms, —CF₃, —NO₂ —C≡N, halogen, alkoxy of up to 8 carbon atoms and —CO₂-alkyl of up to 8 carbon atoms, R₃₄ is hydrogen, alkyl of 1 to 3 carbon atoms or —C≡CH;

p)

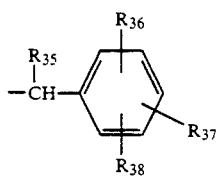

in which R₃₅ is selected from the group consisting of hydrogen, alkyl of 1 to 3 carbon atoms, —C≡N, —C≡CH and —CF₃, R₃₆ and R₃₈ are individually selected from the group consisting of hydrogen, alkyl of 1 to 3 carbon atoms optionally substituted by at least one halogen, alkenyl of 2 to 4 carbon atoms and halogen and R₃₇ is phenyl optionally substituted by at least one alkyl of 1 to 3 carbon atoms or by at least one halogen, R' is selected from the group consisting of hydrogen, saturated or unsaturated alkyl of 1 to 18 carbon atoms optionally substituted by at least one identical or different functional groups, or R' is cycloaliphatic of 3 to 7 carbon atoms substituted by at least one identical or different functional group, or R' is aryl of 6 to 14 carbon atoms optionally substituted by at least one identical or different functional group, or R' is heterocyclic optionally substituted by at least one identical or different functional group, in the form of mixtures of isomers or separate isomers at the level of the cyclopropane ring comprises reacting an ester of the formula

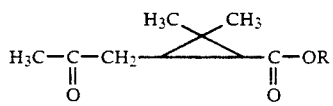

in which R is defined as above with a halogenation agent to obtain a compound of the formula

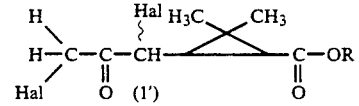

in which R is defined as above, and Hal is halogen in the form of a mixture of isomers at the level of the carbon atom in position 1' and treating the latter with a basic agent in the presence of a compound of the formula R'—OH, in which R' is defined as above to obtain the corresponding compound of formula I.

When R is a cleavable ester, it may be any known remainder such as alkyl of 1 to 18 carbon atoms like methyl, ethyl, n-propyl, isopropyl, n-butyl, isobutyl or preferably, terbutyl, or alkyl as defined above substituted by at least one halogen, preferably chlorine or bromine such as bromo- or chloromethyl, mono-, di- or tri- bromo or chloro ethyl; a silylated alkyl of alkyl of 1 to 4 carbon atoms such as trialkylsilyl methyl, for example terbutyldimethylsilylmethyl or arylalkylsilylmethyl such as diphenylterbutylsilylmethyl. It can also be alkyl substituted by an O-alkyl, O-aryl or O-aralkyl, alkyl preferably of 1 to 4 carbon atoms, aryl of 6 to 14 carbon atoms and preferably phenyl or tolyl and aralkyl preferably benzyl or phenethyl.

It should merely be noted that the remainder of the above ester is such that it is cleavable in an acidic or neutral medium.

When R is benzyl substituted by one or more alkyl, they are preferably methyl, ethyl, propyl or isopropyl. When R is benzyl substituted by one or more alkenyl, they are preferably vinyl, allyl, 2-methylallyl or isobutenyl. When R is benzyl substituted by one or more alkenyloxy, they are preferably vinyloxy, allyloxy, 2-methylallyloxy or isobutenyloxy. When R is benzyl substituted by one or more alkadienyl, they are preferably butadienyl or pentadienyl. When R is benzyl substituted by one or more halogen, they are preferably chlorine, bromine or fluorine.

When R₂ is aryl, it is preferably phenyl and R is then preferably 5-benzyl-3-furylmethyl.

R₃ can particularly be —CH₂—CH=CH₂, CH₂—CH=CH—CH₃, —CH₂—CH=CH—CH=CH₂, —CH₂—CH=CH—CH₂—CH₃ or —CH₂—C≡CH.

B particulary is oxygen and the corresponding group is then preferably 3-phenoxybenzyl, α-cyano-3-phenoxyphenyl, α-ethynyl-3-phenoxybenzyl, 1-(3-phenoxyphenyl)-ethyl or α-thioamido-3-phenoxybenzyl. B also may be —CO— and the corresponding group is then preferably 3-benzoylbenzyl.

When R₁₄ is alkyl, it is preferably methyl, ethyl, linear or branched propyl, linear or branched butyl.

When R₁₄ is alkenyl, it is vinyl, allyl, butenyl, pentenyl or hexenyl. When R₁₄ is alkynyl, it is preferably ethynyl, propargyl or butynyl. When R₁₇ is alkyl, it is methyl, ethyl, linear or branched propyl or linear or branched butyl. When R₁₇ is alkoxy, it is methoxy, ethoxy, linear or branched propoxy or linear or branched butoxy. When R₁₇ is alkylthio, it is methylthio, ethylthio, linear or branched propylthio or linear or branched butylthio. When R₁₇ is alkylsulfonyl, it is corresponding to any one of the above alkylthio.

When R₂₁ is alkyl, it is methyl, ethyl, propyl or isopropyl and preferably methyl. When one or more of $R_{20}$, $R_{22}$ and $R_{23}$ or $R_{19}$, $R_{20}$, $R_{22}$ and $R_{23}$ is halogen, it is preferably fluorine, chlorine or bromine. When $R_{20}$, $R_{22}$ and $R_{23}$ or $R_{19}$, $R_{20}$, $R_{22}$ and $R_{23}$ are alkyl, it is preferably methyl, ethyl, propyl, isopropyl, butyl, isobutyl or n-pentyl.

When one or more of $R_{20}$, $R_{22}$ and $R_{23}$ or $R_{19}$, $R_{20}$, $R_{22}$ and $R_{23}$ are aryl, it is preferably phenyl optionally substituted by alkyl or alkoxy of 1 to 8 carbon atoms, or nitro, trifluoromethyl, hydroxy, halogen or amino. When one or more of the $R_{20}$, $R_{22}$ and $R_{23}$ or $R_{19}$, $R_{20}$, $R_{22}$ and $R_{23}$ are aralkyl, it is preferably benzyl. When one or more $R_{20}$, $R_{22}$ and $R_{23}$ or $R_{19}$, $R_{20}$ $R_{22}$ and $R_{23}$ are —$CO_2$-alkyl or alkoxy, by alkyl is preferably meant methyl, ethyl, propyl or isopropyl and by alkoxy, methoxy, ethoxy, propoxy or isopropoxy.

When $R_{32}$ and $R_{33}$ is saturated or unsaturated, linear, branched or cyclic alkyl, it is preferably methyl, ethyl, n-propyl, isopropyl, cyclopropyl, cyclopropylmethyl, butyl, isobutyl, terbutyl, cyclobutyl, n-pentyl, cyclopentyl, n-hexyl or cyclohexyl, or allyl, propargyl or butynyl. When these groups are substituted by at least one halogen, halogen means fluorine, chlorine, bromine or iodine. When $R_{32}$ or $R_{33}$ is aryl, it is preferably phenyl. When $R_{33}$ is halogen, it is preferably fluorine, chlorine or bromine. When $R_{33}$ is alkoxy, it is preferably methoxy, ethoxy, propoxy or isopropoxy. When $R_{33}$ is $CO_2$-alkyl, alkyl is preferably methyl, ethyl, linear or branched propyl or linear or branched butyl.

When $R_{34}$ is alkyl, it is preferably methyl. When $R_{33}$ is alkyl, it is preferably methyl.

When $R_{36}$ and/or $R_{38}$ is alkyl, it is preferably methyl or ethyl. When the alkyl is substituted by at least one halogen, halogen is preferably fluorine, chlorine and bromine. When $R_{36}$ and/or $R_{38}$ is alkenyl, it is preferably vinyl or allyl. When $R_{37}$ is phenyl substituted by an alkyl or by halogen, alkyl and halogen are preferably the corresponding groups mentioned above for $R_{36}$ and $R_{38}$.

When R' is linear or branched alkyl, alkyl means, for example, methyl, ethyl, linear or branched propyl, linear or branched butyl, linear or branched hexyl, linear or branched decyl, linear or branched tetradecyl, linear or branched octadecyl. When R' is linear or branched unsaturated alkyl, unsaturated alkyl means ethenyl, propenyl, linear or branched butenyl, linear or branched hexenyl, linear or branched decenyl, linear or branched tetradecenyl, linear or branched octadecenyl, or also unsaturated aliphatic containing two or more double bonds.

When R' is alkyl substituted by at least one or more functional group, functional group preferably means halogen, —OH or —SH, —$OR_a$ or —$SR_a$ in which $R_a$ is alkyl of 1 to 8 carbon atoms, and —$NO_2$ or

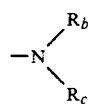

in which $R_b$ and $R_c$ individually are hydrogen or alkali of 1 to 8 carbon atoms, $C\equiv N$, —$SO_3H$ or —$PO_4H_2$ or —$COalk_1$, —$SO_2alk_2$ or —$SO_3alk_3$ in which $alk_1$, $alk_2$ and $alk_3$ are alkyl of 1 to 18 carbon atoms. R' can also be alkyl substituted by aryl such as benzyl or phenethyl substituted by at least one —OH, —Oalk or alk of 1 to 8 carbon atoms, —$CF_3$, —$OCF_3$, —$SCF_3$ or

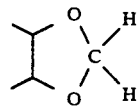

R' can also be alkyl substituted on 2 adjacent carbons by a group

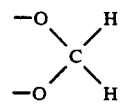

or substituted by

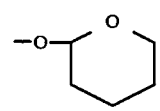

When R' is alkyl substituted by one or more functional groups, the following can be mentioned as preferred values of R': —$(CH_2)_n$—$CHal_3$ in which n is an integer from 1 to 8 and Hal is halogen, for example —$CH_2$—$CCl_3$, —$CH_2$—$CF_3$, —$CH_2$—$CH_2$—$CCl_3$ or—$CH_2$—$CH_2$—$CF_3$, —$(CH_2)_{n1}$—$CHHal_2$ in which Hal is defined as above and n1 is a number from 0 to 8, for example —$CH_2$—$CHCl_2$, —$CH_2$—$CHF_2$ or —$CHF_2$, —$(CH_2)_n$—$CH_2Hal$ in which n and Hal are defined as above, for example —$CH_2$—$CH_2Cl$ or —$CH_2$—$CH_2F$, —$C(CHal_3)_3$ in which Hal is defined as above, for example

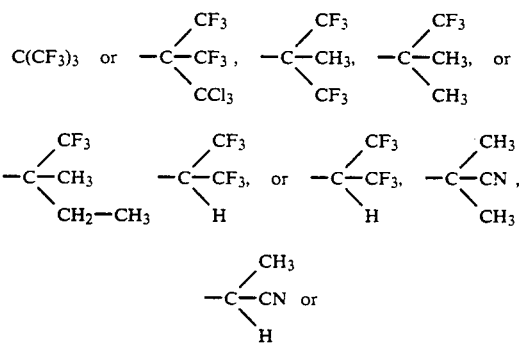

—$(CH_2)_n$—CN, in which n is defined as previously,

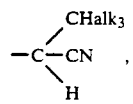

in which Hal is defined as previously, for example

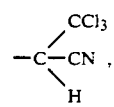

—$(CH_2)_n$—$OR_d$ in which n is defined as previously and $R_d$ is hydrogen or alkyl of 1 to 8 carbon atoms, for example the —CH$_2$—OCH$_3$, —CH$_2$—CH$_2$—O—CH$_3$, —CH$_2$—CH$_2$—O—CH$_2$—CH$_3$ or —CH$_2$—CH$_2$—OH,

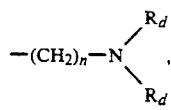

in which n and R$_d$ are defined as previously and the two R$_d$ s can be different from each other, for example

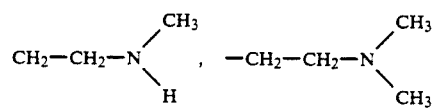

or

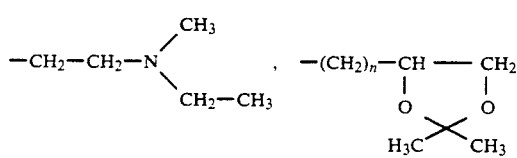

in which n is defined as previously, for example

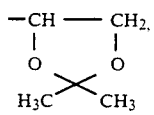

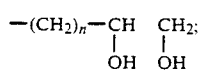

in which n is defined as previously, for example

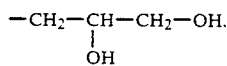

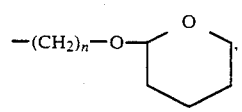

in which n is defined as previously, for example

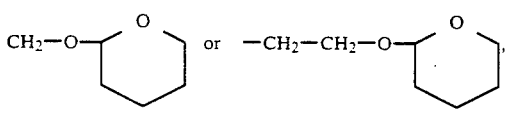

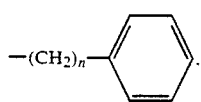

in which n is defined as previously, for example benzyl or phenethyl,

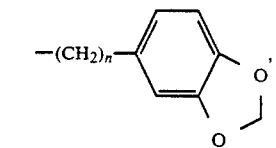

in which n is defined as previously, for example the

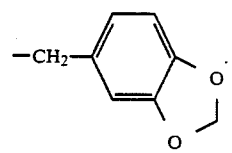

When R' is cycloaliphatic of 3 to 7 carbon atoms, it is cyclopropyl, cyclobutyl, cyclopentyl, cyclohexyl or cycloheptyl, optionally linked to the oxygen atom by alkyl of 1 to 3 carbon atoms, notably methyl. When R' is cycloaliphatic of 3 to 7 carbon atoms substituted by at least one or more functional groups, functional group preferably means halogen, alkyl of 1 to 6 carbon atoms, alkoxy of 1 to 6 carbon atoms, or —NO$_2$.

When R' is optionally substituted aryl, it is preferably phenyl or phenyl substituted by at least one or more OH, Oalk or alk, alk is alkyl of 1 to 8 carbon atoms, or —CF$_3$, —OCF$_3$ or —SCF$_3$ or at least one or more halogen. When R' is optionally substituted heterocyclic, it is preferably pyridyl, furyl, thiophenyl, oxazolyl or thiazolyl optionally substituted by one or more of the above groups.

The process of the invention has a remarkably general nature. It allows both cleavable esters, therefore intermediate esters, which can be converted into biologically-active esters by standard processes of transesterification or hydrolysis followed by an esterification, to be obtained, as well as biologically-active esters to be obtained directly.

It has in addition a remarkable selectivity, insofar as it leads to compounds of formula I of (Z) configuration, that is to say to the biologically-active form of these compounds.

A particular subject of the invention is a process wherein the halogenation agent is a chlorination or bromination agent, the latter being more preferred. Among the halogenation agents of the invention are bromine used on its own or on a polymer support, chlorine, N-bromo and N-chloro succinimides and the N-bromo and N-chloro acetamides, pyridinium perbromide, pyridinium hydrobromide perbromide, pyridinium hydrochloride perchloride, phenyltrimethylammoniumperbromide, 2-carboxyethyltriphenylphosphoniumperbromide, 2-hydropyrrolidone tribromide, cupric bromide and chloride, 5,5-dibromo 2,2-dimethyl 4,6-dioxo 1,3-dioxane, phosphorous tri and penta bromide and chloride, trimethylbromo and trimethylchloro silane—DMSO—tertiary amine mixtures and ferric chloride. The preferred agents are bromine, chlorine, N-bromo and N-chloro succinimides and acetamides, pyridinium perbromide and perchloride, pyridinium hydrobromide and hydrochloride perbromide and perchloride.

The halogenation reaction is carried out in a solvent which can be a halogenated solvent, particularly methylene chloride, chloroform, carbon tetrachloride, dichloroethane, or a mixture of these, an ether such as tetrahydrofuran, dimethoxyethane, methyl terbutylether or dioxane, an aromatic solvent such as benzene, toluene, xylene or a corresponding saturated solvent, in particular cyclohexane, an alcohol such as methanol or ethanol, ethyl acetate or also dimethylformamide or dimethylsulfoxide.

It is advantageous to limit to the maximum the formation of mono- and trihalogenated derivatives, alongside the expected derivative of formula III, and thus a subject of the invention is a process wherein approximately 2 equivalents of the halogenation agent are used.

Under the preferred conditions of the invention, the basic agent used is selected from the group consisting hydrides, alcoholates, amides, alkali metal and alkaline-earth metal carbonates, particularly sodium or potassium, tertiary amines, particularly triethylamine, pyridine or dimethylaminopyridine.

The operation is carried out in a solvent which is either the compound of formula R'—OH, or a mixture of this compound with a suitable cosolvent. This can be preferably, a halogenated solvent, an ether, an aromatic solvent or a corresponding saturated solvent such as those which were mentioned above, or also dimethylformamide or dimethylsulfoxide. The operation is carried out at a temperature compatible with the solvent used which can range from $-78°$ C. to $+40°$ C. aproximately.

A particular subject of the invention is a process as defined previously wherein R is a remainder of a cleavable ester in an acidic or neutral medium chosen from the group consisting of alkyl of 1 to 18 carbon atoms, alkyl of 1 to 18 carbon atoms substituted by one or more halogen, alkyl of 1 to 4 carbon atoms substituted by a silylated group and alkyl of 1 to 4 carbon atoms substituted by one of the following: O-alkyl, O-aryl or O-aralkyl, alkyl of 1 to 4 carbon atoms and aryl of 6 to 14 carbon atoms.

A preferred process is that wherein R is a remainder of a cleavable ester in an acidic or neutral medium chosen from the group consisting of alkyl of 1 to 4 carbon atoms, alkyl of 1 to 4 carbon atoms substituted by one or more chlorine or bromine, alkyl of 1 to 4 carbon atoms substituted by alkylsilyl and alkyl of 1 to 4 carbon atoms substituted by O-alkyl, O-aryl or O-aralkyl, as defined above.

A particular subject of the invention is a process as defined previously wherein R is alkyl of 1 to 4 carbon atoms, preferably terbutyl, or methyl or ethyl substituted by one or more chlorine or bromine, preferably bromo or chloro methyl or a mono-, di- or tribromo or chloroethyl.

Also a particular subject of the invention is a process as defined previously wherein R is an ester remainder selected from the group consisting of benzyl substituted by one or more halogen,

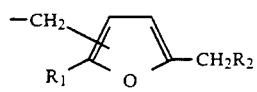

in which $R_1$ and $R_2$ are defined as previously,

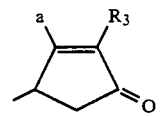

in which a and $R_3$ are defined as previously,

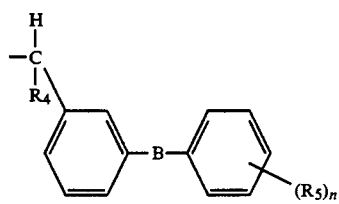

in which $R_4$, $R_5$ and n are defined as previously,

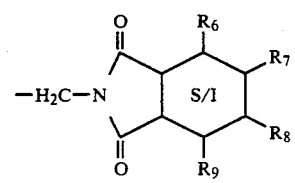

in which $R_6$, $R_7$, $R_8$, $R_9$ and S/I are defined as previously,

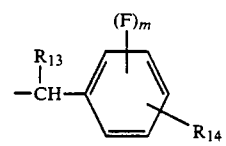

in which $R_{13}$, $R_{14}$ and m are defined as previously,

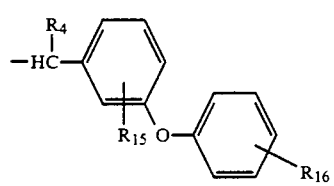

in which $R_4$, $R_{15}$ and $R_{16}$ are defined as previously,

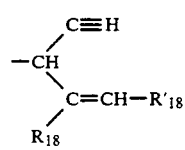

in which $R_{18}$ and $R'_{18}$ are defined as previously and

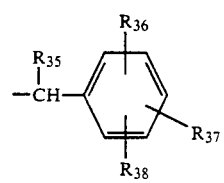

in which $R_{35}$, $R_{36}$, $R_{37}$ and $R_{38}$ are defined previously.

A more particular subject of the invention is a process as defined previously wherein R is an ester remainder selected from the group consisting of benzyl substituted by 1 to 5 fluorine atoms,

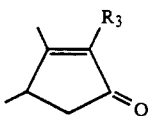

in which $R_3$ is a —$CH_2$—CH—$CH_2$ or —$CH_2$—C≡CH,

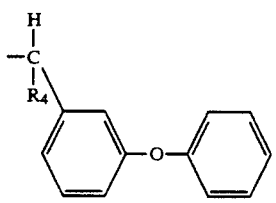

in which $R_4$ is defined as previously,

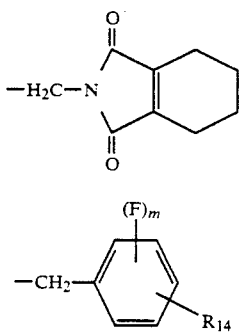

in which $R_{14}$ and m are defined as previously,

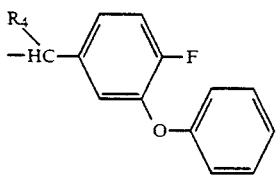

in which $R_4$ is defined as previously,

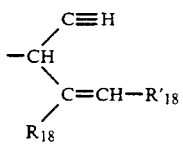

in which $R_{18}$ and $R'_{18}$ are defined as previously,

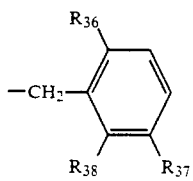

in which $R_{36}$ is hydrogen, fluorine or chlorine, $R_{37}$ is phenyl or 3-fluorophenyl and $R_{38}$ is hydrogen, fluorine or chlorine or methyl.

Also a particular subject of the invention is a process as defined previously wherein a compound of formula R'—OH is used at the start in which R' is hydrogen or alkyl or cycloalkyl of 1 to 8 carbon atoms, and particularly ethyl, terbutyl or also cyclo-propyl or cyclopropylmethyl, alkyl of 1 to 8 carbon atoms substituted by one or more halogen, and particularly by one or more fluorine, $(CH_2)_m$—O—$(CH_2)_n$—$CH_3$ in which m is an integer which can vary from 1 to 8 and n is an integer which can vary from 0 to 8, and particularly —$CH_2$—O—$CH_3$.

A quite particular subject of the invention is a process as defined previously wherein a compound of formula II of (1R,cis) structure in which R is a remainder of (R,S) or (S) α-cyano 3-phenoxybenzyl alcohol or a remainder of (R,S) or (S) α-cyano 4-fluoro 3-phenoxybenzyl alcohol and a compound of formula R'—OH in which R' is methyl, ethyl, terbutyl or 1,1,1,3,3,3-hexafluoropropyl are used at the start.

The intermediate compounds of formula III are new compounds and therefore a subject of the invention is also the said compounds of formula III in the form of isomer mixtures or separate isomers at the level of the cyclopropane ring.

The compounds of formula I are for the most part known and described in the European Patents or European Applications Nos. 38271, 41021, 48186, 110769, 114012, 215701, 357742, 300898, 176387, 261035, 381563 or in the French Patent 2,612,184. They are biologically-active compounds possessing generally, pesticide properties, notably insecticide and acaricide properties, or are intermediate compounds in the synthesis of active compounds.

The compounds of formula I in which R is methyl substituted by bromine or chlorine or ethyl substituted by 1, 2 or 3 bromine or chlorine atoms are cleavable esters, and therefore intermediate compounds in the synthesis of biologically-active esters. They have not been described up to now and also are one of the subjects of the invention.

The cleavage of the esters of formula I, which are intermediate compounds in the synthesis of biologically-active esters, can be carried out by methods known to a one skilled in the art. Examples are given in the European Patent No. 48186 already mentioned above, or, in a general way, in the work of T. W. GREENE: "Protective Groups in Organic Synthesis".

The compounds of formula II used at the start of the process of the invention can be obtained by a process such as those described hereafter in the experimental part, that is to say by esterification of the corresponding acid by the appropriate alcohol. These compounds of formula II, with the exception of those in which R is methyl, ethyl, 3-phenoxybenzyl or α-cyano 3-phenoxybenzyl, are new compounds and as such are one of the subjects of the invention.

The acid mentioned above, in any one of its configurations, is known or can be prepared by a process known to one skilled in the art. The (1R,cis) acid is described in Agr. Biol. Chem., Vol. 29, No. 8, p. 784 (1965); the (1S,cis) acid can be prepared by the process described in U.S. Pat. No. 4,296,038; the (1R,trans) acid can be prepared according to the process described in Synth. Comm., (1984) Vol. 14, p. 1239–46 and the (1S,trans) acid by the same process starting with (—)

3-carene; the (1R,S cis) acid can be prepared by the processes described in the above reference Agr. Biol. Chem., or U.S. Pat. No. 4,296,038, starting with the racemic 3-carene, which can be obtained according to the method described in J. Org. Chem. (1987), Vol. 52, p. 1493 or in Tet. Letters, (1984), p. 5255; the (1R,S trans) acid, as well as the (1R,S cis) acid, can be obtained by the process described in Japan Kokai J81 079644.

The compounds of formula II in which R is methyl, 3-phenoxybenzyl and α-cyano 3-phenoxybenzyl are described in Synth. Comm. (1988), Vol. 18, p. 1139–49 and Tetrahedron (1986), Vol. 42, p. 5717–28.

In the following examples, there are described several preferred embodiments to illustrate the invention. However, it should be understood that the invention is not intended to be limited to the specific embodiments.

EXAMPLE 1 methyl (1R,cis) 2,2-dimethyl-3-[(Z) 2-(methoxycarbonyl) ethenyl]-cyclopropane 1-carboxylate.

Step A: methyl (1R,cis) 2,2-dimethyl 3-(1,3-dibromo 2-oxopropyl)-cyclopropane 1-carboxylate.

2.4 g of methyl (1R,cis) 2,2-dimethyl-3-(2-oxopropyl) cyclopropane 1-carboxylate and 30 ml of methylene chloride were mixed together under an inert gas atmosphere and after the mixture was cooled to +10° C., 1.3 ml of bromine were added. The mixture was stirred for 2 hours at ambient temperature and then the medium was poured on a water - ice mixture. Extraction was carried out with methylene chloride and the organic phase was dried and evaporated to dryness. The residue was chromatographed on silica, eluting with a methylene chloride - hexane mixture (7-3) to obtain 3.2 g of expected product.

Analysis: $C_{10}H_{14}Br_2O_3$; molecular weight = 342.04
Calculated: C % 35.11 H % 4.12 Br % 46.72 Found: 35.0 4.2 46.5

IR Spectrum (CHCl₃): Absorptions at 1736, 1719 $cm^{-1}$ (C=O), 1438 $cm^{-1}$ (COOCH₃)

NMR Spectrum (CDCl₃ 250 MHz ppm): 1.22 (s), 1.27 (s), 1.34 (s): CH₃ twinned; 1.84 (d) and 1.98 (m): H₁ and H₃ cis; 3.63 (s), 3.73 (s): CO₂CH₃; 5.50 (d, J=11), 5.67 (d, J=11) Hal-CH-CH.

Step B: methyl (1R,cis) 2,2-dimethyl-3-[(Z)-2-(methoxy-carbonyl) ethenyl]-cyclopropane-1-carboxylate.

0.16 g of sodium methylate and 1.6 ml of methanol were mixed together under an inert gas atmosphere and after the mixture was cooled to about 0° C., 0.5 g of methyl (1R,cis) 2,2-dimethyl-3-(1,3-dibromo-2-oxopropyl)-cyclopropane-1-carboxylate in solution in 2.5 ml of methanol were slowly added. The mixture was stirred at about −5° C. for 90 minutes and then the solvent was evaporated under reduced pressure at about 30° C. and 10 ml of methylene chloride were added. The solution was washed with water, dried and concentrated to dryness to obtain 0.324 g of crude product which was chromatographed on silica, eluting with a cyclohexane - ethyl acetate mixture (6-4) to obtain 0.262 g of the expected product.

IR Spectrum (CHCl₃): Absorptions at 1720 $cm^{-1}$ (C=O); 1634 $cm^{-1}$ (C=C). Compatible with the Z isomer.

NMR Spectrum (CDCl₃ 250 MHz ppm): 1.28 (s), 1.31 (s): CH₃ twinned; 1.96 (d, J=3.5), 3.25 (dd): H₁/H₃ cis; 3.46 (s), 3.72 (s): CH₃ ester in position 3; 5.90 (dd), 6.65 (dd): H in position 1'-Z Isomer.

EXAMPLE 2 methyl (1R,cis) 2,2-dimethyl-3-[(Z) 2-terbutoxycarbonyl) ethenyl]-cyclopropane 1-carboxylate (product A) and methyl (1R,cis) 2,2-dimethyl-3-[(Z) 2-carboxyethenyl)-cyclopropane 1-carboxylate (product B).

12 ml of dimethoxyethane and 0.684 g of potassium terbutylate were mixed together under an inert gas atmosphere and a solution of 0.684 g of methyl-(1R,cis) 2,2-dimethyl-3-(1,3-dibromo-2-oxopropyl)-cyclopropane-1-carboxylate of Step A of Example 1 in 10 ml of dimethoxyethane was slowly added to the mixture. Then, the mixture was stirred for 40 minutes at about −60° C. and 3 ml of dimethoxyethane and 2 ml of terbutanol were added. The mixture was stirred at about −60° C. for 15 minutes and after water and methylene chloride were added, followed by decanting, the aqueous phase was extracted with methylene chloride. The combined organic phases were washed with water, dried and concentrated to dryness at about 30° C. to obtain 0.219 g of the expected product A.

The combined aqueous phases were acidified with 2N hydrochloric acid and extraction was carried out with methylene chloride. The organic phase was concentrated to dryness to obtain 0.211 g of product B, corresponding to crude methyl (1R,cis) 2,2-dimethyl-3-[(Z)2-carboxy-ethenyl]-cyclopropane-carboxylate. Products A and B were chromatographed on silica, eluting with mixtures of methylene chloride - hexane (8-2) and cyclohexane - ethyl acetate (6-4) respectively.

Analyses of product A:

IR Spectrum (CHCl₃): Absorptions at 1721 $cm^{-1}$ (shoulder at 1705 $cm^{-1}$) (C=O), 1631 $cm^{-1}$ (C=C), 1439 $cm^{-1}$ (O—CH₃), 1368 $cm^{-1}$ (O—tBu)

NMR Spectrum (CDCl₃ 250 MHz ppm): 1.27 (s) and 1.31 (s): CH₃ twinned; 1.49: —CO₂tBu; 1.92 (d, J=8.5) and 3.26 (m): H₁ and H₃ cis; 3.65: O—CH₃; 5.80 (d, J=11.5): CH=alpha of CO; 6.51 (dd, J=10.5–11.5): CH= beta of CO. delta Z.

Analyses of product B:

IR Spectrum (CHCl₃): Absorptions at 3518 $cm^{-1}$ (acid OH), 1723-1693 $cm^{-1}$ (C=O), 1628 $cm^{-1}$ (C=C), 1440 $cm^{-1}$ (COOMe)

NMR Spectrum (CDCl₃ 250 MHz ppm): 1.28 (s) and 1.32 (s): CH₃ twinned; 1.99 (d) and 3.21 (m): H₁ and H₃ cis; 3.67 (s): CO₂CH₃; 5.92 (d, J=11) and 6.77 (dd): CO—CH=CH—CH; 11.6 (m): mobile 1H.

EXAMPLE 3 methyl (1R,cis) 2,2-dimethyl-3-[(Z) 2-[(1,1,1,3,3,3-hexafluoro)-propoxycarbonyl]-ethenyl]-cyclo-propane-1-carboxylate 0.057 g of sodium hydride suspended at 50% in oil were washed under an inert gas atmosphere with cyclohexane, then 1 ml of dimethoxyethane was added. 0.33 g of hexafluoroisopropanol in 1 ml of dimethoxyethane were added to the suspension and the mixture was stirred for 30 minutes. The solution was cooled to +5° C. and a solution of 0.173 g of methyl (1R,cis) 2,2-dimethyl-3-(1,3-dibromo 2-oxopropyl)-cyclopropane-1-carboxylate in 1 ml of dimethoxyethane was added slowly. The mixture was stirred for one hour at +3°/+5° C., and was poured into an aqueous solution of 1N hydrochloric acid and extracted with methylene chloride. The organic phase was dried and concentrated to dryness. The residue was chromatographed on silica, eluting with a mixture of methylene chloride - hexane (7-3) to obtain 0.16 g of the expected product.

NMR Spectrum (CDCl$_3$ 250 MHz): 1.30 (s), 1.34 (s): CH$_3$ twinned; 3.68 (s): CH$_3$ ester; 2.06 (d, J=8.5): H$_1$; 3.12 (dd): H$_3$; 6.99 (dd): H'$_1$; 6.00 (d, J=11.5): H'$_2$; 5.81: >CH—.

EXAMPLE 4 methyl (1R,cis) 2,2-dimethyl 3-[(Z) 2-(1,1,1,3,3,3-hexafluoro)-propoxycarbonyl]-ethenyl]-cyclopropane-1-carboxylate.

1.5 ml of dimethoxyethane, 0.056 g of potassium terbutylate and 0.2 g of hexafluoroisopropanol were mixed together under an inert gas atmosphere and then a solution of 0.170 g of methyl (1R,cis) 2,2-dimethyl-3-(1,3-dibromo 2-oxopropyl)-cyclopropane-1-carboxylate in 0.5 ml of dimethoxyethane was added at 5° C. The mixture was stirred for 18 hours at ambient temperature and after N hydrochloric acid was added, extraction was carried out with methylene chloride. The extracts were dried and concentrated to dryness. The residue was chromatographed on silica, eluting with a methylene chloride-hexane mixture (7-3) to obtain 0.066 g of the expected product.

IR Spectrum (CHCl$_3$): Absorptions at 1758, 1740 and 1718 cm$^{-1}$ (>C=O), 1624 cm$^{-1}$ (C=C)

EXAMPLE 5 methyl (1R,cis) 2,2-dimethyl-3-[(Z) 2-(1,1,1,3,3,3-hexafluoro)-propoxycarbonyl]-ethenyl]-cyclopropane-1-carboxylate.

Using the procedure of Example 4, 0.027 g of sodium methylate instead of potassium terbutylate were reacted to obtain the expected product which was identical to that of Example 4.

EXAMPLE 6 methyl (1R,cis) 2,2-dimethyl-3-[(Z) 2-carboxyethenyl] -cyclopropane 1-carboxylate.

1 ml of a 1N solution of potassium carbonate was placed under an inert gas atmosphere and then a solution of 0.342 g of methyl (1R,cis) 2,2-dimethyl-3-(1,3-dibromo-2-oxopropyl)-cyclopropane-1-carboxylate in 1.5 ml of tetrahydrofuran was added at about +5° C. The mixture was stirred for 90 minutes and then the temperature was allowed to rise to 20° C. and stirring was continued for 4 hours. Water was added and extraction was carried out with methylene chloride. The organic phase was dried and the solvent was evaporated. The residue was chromatographed on silica, eluting with a methylene chloride - ethanol mixture (97-3) to obtain 0.046 g of the expected product.

NMR Spectrum (CDCl$_3$ 250 MHz): 1.28 (s), 1.32 (s): CH$_3$ twinned; 1.98 (d, J=8.5), 3.20 (m): H$_1$/H$_3$ cis; 3.67 (s): CH$_3$ ester; 5.91 (d, J=11.5), 6.77 (dd, J=11.5): H (C=C).

EXAMPLE 7

(S) α-cyano-3-phenoxybenzyl (1R,cis) 2,2-dimethyl-3-[(Z) 2-(methoxycarbonyl)-ethenyl]-cyclopropane-1-carboxylate Step A: (S) α-cyano-3-phenoxybenzyl (1R,cis) 2,2-dimethyl-3-(1,3-dibromo-2-oxopropyl)-cyclopropane-1-carboxylate.

1.75 g of (S) α-cyano 3-phenoxybenzyl 2,2-dimethyl-3-(2-oxopropyl)-cyclopropane-1-carboxylate and 17.5 ml of tetrahydrofuran were mixed together under an inert gas atmosphere and 3.29 g of pyridinium hydrobromide perbromide were added slowly at 0°,+5° C. The mixture was stirred for 6 hours at +5° C. and then stood in an ice-box overnight and filtered. The filtrate was concentrated to dryness at 25° C. under reduced pressure and the product was purified on silica, eluting with a methylene chloride - hexane mixture (7-3) to obtain 0.8 g of the expected product.

Analysis: C$_{23}$H$_{20}$NO$_4$Br$_2$; molecular weight=535.2
Calculated: C % 51.6 H % 3.8 Br % 29.9 N % 2.6
Found: 51.4 4.0. 29.4 2.5

NMR Spectrum (CDCl$_3$ 250 MHz): Mixture of isomers at the level of the bromine in position 1'. 1.16-1.-23-1.25-1.27: twinned DiMe; 1.88: H$_1$; 2.07: H$_3$ of the cyclopropyl; 6.25 and 6.38:

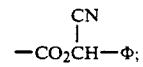

4.06 (d) and 4.39 (d): —CH$_2$Br—CO—; 5.20 (d) and 5.36 (d): CHBr—CO; 6.95 to 7.45: aromatic H's.

The starting ester was obtained as follows:

15 ml of methylene chloride, 2 g of 2,2-dimethyl 3-(2-oxopropyl)-cyclopropane-1-carboxylic acid, 2.59 g of dicyclohexylcarbodiimide and 2.8 ml of pyridine were mixed together under an inert gas atmosphere and then a mixture of 2.74 g of (S)-α-cyano-3-phenoxybenzyl alcohol, 20 ml of methylene chloride and 0.02 g of 4-dimethylaminopyridine were added over 20 minutes at +10° C. The mixture was stirred at 20° C. for 20 hours, followed by filtering, and the filtrate was concentrated to dryness under reduced pressure at 30° C. The residue was chromatographed on silica, eluting with a cyclohexane - ethyl acetate mixture (8-2) to obtain 3.71 g of the expected product.

IR Spectrum (CHCl$_3$): Absorptions at 1736 cm$^{-1}$ (carbonyl), 1588 and 1498 cm$^{-1}$ (phenoxy). Absence of acid and of OH.

NMR Spectrum (CDCl$_3$ 250 MHz): 1.11 (s) and 1.21 (s): twinned diMe; 1.63 (m): H$_1$ and H$_3$ cis; 2.16 (s): CH$_3$ in α-position of the carbonyl; 2.87 (m): CH$_2$ in α-position of the carbonyl, 6.27 (s):

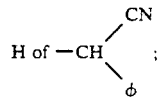

7.00 to 7.45 (9H): aromatics.

Circular dichroism (dioxane): Max. 225 nm Δε=+1; 281 nm Δε=+0.3; 288 nm: Δε=+0.3; 300 nm Δε=+0.07.

Step B: (S) α-cyano-3-phenoxybenzyl (1R,cis) 2,2-dimethyl-3-[(Z) 2-(methoxycarbonyl)-ethenyl]-cyclopropane-1-carboxylate.

0.165 g of sodium methylate and 3 ml of methanol were mixed together under an inert gas atmosphere and then 0.770 g of the product of Step A and 6 ml of methanol were added at 5° C. The mixture was stirred for one hour at 0° C., then for 2 hours 30 minutes at ambient temperature and the reaction medium was poured into 25 ml of 2N hydrochloric acid at about +5° C. Extraction was carried out with methylene chloride and the extracts were washed with water and dried. After evaporation of the solvent, 0.6 g of crude product were obtained which was purified by chromatography on silica and eluting with a methylene chloride - hexane mixture (8-2), then (7-3) to obtain 0.267 g of a mixture containing the expected product.

EXAMPLE 8

(R,S) α-cyano-3-phenoxybenzyl (1R,cis) 2,2-dimethyl-3-[(Z) 2-methoxycarbonyl)-ethenyl]-cyclopropane-1-carboxylate.

Step A: (R,S) α-cyano-3-phenoxybenzyl (1R,cis 2,2-dimethyl-3-(1,3-dibromo-2-oxopropyl)-cyclopropane-1-carboxylate.

0.380 g of (RS) α-cyano-3-phenoxybenzyl (1R,cis) 2,2-dimethyl-3-(2-oxopropyl)-cyclopropane-1-carboxylate and 4 ml of carbon tetrachloride were mixed together under an inert gas atmosphere and then 102 μl of bromine in 1 ml of carbon tetrachloride was added slowly at about 15° C. The mixture was stirred for 4 hours and after concentrating to dryness at about 30° C., 0.530 g of crude expected product was obtained, which was used as is for the following stage. The product could be purified by chromatography on silica, eluting with a methylene chloride - hexane mixture (8-2).

NMR Spectrum (CDCl$_3$ 250 MHz ppm): 1.16-1.23-1.25-1.27: CH$_3$ twinned; 1.88-2.07: H$_1$ and H$_3$ cis; 4.06 (d) and 4.39 (d), 4.22: —CO—CH$_2$Br; 5.20 (d) and 5.36 (d): —CO—CH—Br; 6.25 and 6.38: CO$_2$—CH—CN; 6.95 to 7.45: aromatics.

The starting ester was prepared as follows:

0.344 g of 2,2-dimethyl-3-(2-oxopropyl)-cyclopropane-1-carboxylic acid, 3 ml of methylene chloride, 0.48 ml of pyridine and 0.445 g of dicyclohexylcarbodiimide were mixed together and then a solution of 0.471 g of (RS) α-cyano-3-phenoxybenzyl alcohol in 2 ml of methylene chloride and a few milligrams of 4-dimethylaminopyridine were added. The mixture was stirred at ambient temperature for 18 hours, filtered and concentrated to dryness at 30° C. The residue was chromatographed on silica, eluting with a cyclohexane - ethyl acetate mixture (75-25) to obtain 0.594 g of the expected product.

NMR Spectrum (CDCl$_3$ 250 MHz ppm): 1.11 to 1.28: CH$_3$ twinned; 1.50 to 1.68: H cyclopropyl; 2.10 (s), 2.16 (s) (3H): —COCH$_3$; 2.85 (m): =C—CH$_2$—CH; 6.27 (s): —CO$_2$—CH—; 7.03 to 7.45: aromatics.

IR Spectrum (CHCl$_3$): Absorptions at 1735, 1712 cm$^{-1}$ (>C=O); 1588, 1498 cm$^{-1}$ (—φ—O—φ—).

Step B: (R,S) α-cyano-3-phenoxybenzyl (1R,cis) 2,2-dimethyl-3-[(Z) 2-methoxycarbonyl)-ethenyl]-cyclopropane-1-carboxylate.

Using the procedure of Step B of Example 7, the dibrominated product of Step A was reacted to obtain after purification under the same conditions as in Step B of Example 7, the expected product.

EXAMPLE 9

(RS) α-cyano-3-phenoxybenzyl (1R,cis) 2,2-dimethyl-3-[(Z) 2-[(1,1,1,3,3,3-hexafluoro)-propoxycarbonyl]-ethenyl]-cyclopropane-1-carboxylate.

0.030 g of sodium hydride suspended as 50% in oil were washed under an inert gas atmosphere with cyclohexane and then 1 ml of dimethoxyethane was added to it. A solution of 0.130 g of hexafluoroisopropanol in 1 ml of dimethoxyethane was added slowly at about 0° C. and the mixture was stirred for 30 minutes at 0°,+5° C. and after cooling to −5° C., a solution of 0.163 g of (RS) α-cyano-3-phenoxybenzyl (1R,cis) 2,2-dimethyl-3-(1,3-dibromo-2-oxopropyl) cyclopropane-1-carboxylate of Step A of Example 8 in 1 ml of dimethoxyethane were added. The whole mixture was stirred for 90 minutes and was poured into a 1N aqueous solution of hydrochloric acid. Extraction was carried out with methylene chloride and the organic phase was dried and evaporated to dryness. The residue was chromatographed on silica, eluting with a methylene chloride - hexane mixture (8-2) to obtain 0.056 g of the expected product.

NMR Spectrum (CDCl$_3$) 250 MHz): 1.26 (s), 1.30 (s), 1.35 (s), 1.36 (s): CH$_3$ twinned; 2.10 (d), 3.21 (m) H$_1$/H$_3$ cis; 5.8 (seven): H of CO$_2$—CH(CF$_3$)$_2$; 6.02 (dm), 6.08 (dm): H in position 2'; 6.32 (s), 6.34 (s): H in α position; 6.8 to 7.5 (m) aromatic H's and H in position 1'.

EXAMPLE 10

(RS) α-cyano-3-phenoxybenzyl (1R,cis) 2,2-dimethyl-3-[(Z) 2-[(1,1,1,3,3,3-hexafluoro-propoxy)-carbonyl]-ethenyl]-cyclopropane-1-carboxylate.

Step A: (RS) α-cyano-3-phenoxybenzyl (1R,cis) 2,2-dimethyl-3-(1,3-dichloro-2-oxopropyl)-cyclopropane-1-carboxylate.

0.300 g of (RS) α-cyano-3-phenoxyphenyl (1R,cis) 2,2-dimethyl-3-(2-oxopropyl) cyclopropane 1-carboxylate of Example 8, 6 ml of chloroform and 160 μl of sulfuryl chloride were mixed together under an inert gas atmosphere and the mixture was stirred at ambient temperature for one hour, then concentrated to dryness to obtain 0.546 g of crude expected product which was used as is for the following stage.

Step B: (RS) α-cyano-3-phenoxybenzyl (1R,cis) 2,2-dimethyl-3-[(Z) 2-[(1,1,1,3,3,3-hexafluoro)-propoxycarbonyl]-ethenyl]-cyclopropane-1-carboxylate.

1 ml of toluene and 0.02 g of sodium hydride at 50% in oil were mixed together under an inert gas atmosphere and then 200 μl of hexafluoro isopropanol and 1 ml of toluene were added slowly. The mixture was stirred for 35 minutes at −10° C. and then 0.1 g of the crude product of Step A in solution in 0.5 ml of toluene was added. The mixture was allowed to return to ambient temperature and was stirred for 2 hours. The solvent was evaporated and the residue was chromatographed on silica, eluting with a cyclohexane - ethyl acetate mixture (85-15) to obtain the expected product which was identical to that of Example 9.

EXAMPLE 11 terbutyl (1R,cis) 2,2-dimethyl-3-[(Z)-2-[(1,1,1,3,3,3-hexafluoropropoxy)-carbonyl]-ethenyl]-cyclopropane-1-carboxylate.

Step A: terbutyl (1R,cis) 2,2-dimethyl-3-(1,3-dibromo-2-oxopropyl)-cyclopropane-1-carboxylate.

0.113 g of terbutyl (1R,cis) 2,2-dimethyl-3-(2-oxopropyl)-cyclopropane-1-carboxylate and 3 ml of tetrahydrofuran were mixed together under an inert gas atmosphere and then 0.34 g of pyridinium hydrobromide perbromide were added at +5° C. The mixture was stirred at ambient temperature for one hour and then was separated and concentrated to dryness. The residue was chromatographed on silica, eluting with a cyclohexane - ethyl acetate mixture (7-3) to obtain 0.165 g of the expected product.

NMR Spectrum (CDCl3 250 MHz ppm): 1.16 to 1.28: CH3 twinned; 1.43 and 1.40: H of tBu; 1.7 to 1.9: $H_1$ and $H_3$; 4.08 (d), 4.36 (d) and 4.29: —CO—CH2—Br; 5.24 (d) and 5.50 (d): CO—CHBr—.

The terbutyl (1R,cis) 2,2-dimethyl-3-(2-oxopropyl)-cyclopropane-1-carboxylate was prepared as follows:

0.17 g of (1R,cis) 2,2-dimethyl-3-(1-oxopropyl)-cyclopropane-1-carboxylic acid and 1.7 ml of ethyl acetate were mixed together under an inert gas atmosphere and then a solution of 0.36 g of terbutyloxy N,N'-diisopropylcarbodiimide in 1 ml of ethyl acetate was added slowly. After 6 hours of stirring at ambient temperature, another 0.15 g of terbutoxy N,N'-diisopropylcarbodiimide was added and stirring was continued for 16 hours. After separation, the solvent was evaporated and the residue was chromatographed on silica, eluting with a cyclohexane - ethyl acetate mixture (7-3) to obtain 0.153 g of the expected product.

IR Spectrum (CHCl3): Absorption at 1712–1368 cm$^{-1}$ (CH3 of tBu) > =0 - Absence of acid.

NMR Spectrum (CDCl3 250 MHz ppm): 1.18 (s) and 1.20 (s): CH2 twinned; 1.35 (m), 1.50 (d, J=8.5): $H_3$ and $H_1$; 1.45 (s) H of tBu; 2.15 (s): H of CH3 in position 3'; 2.79 (dd) and 2.93 (dd): H of CH2 in position 1'.

The terbutyloxy N,N'-diisopropylcarbodiimide was prepared as follows:

20 g of terbutanol and 1.73 g of cuprous chloride were mixed together under an inert gas atmosphere and then 34 g of N,N'-diisopropylcarbodiimide were added at +30°/+35° C. The mixture was stirred while allowing it to return to ambient temperature. After separation, the filtrate was rinsed with isopropyl ether and the solvent was evaporated. The residue was rectified under 4–5 mm of mercury. B.p.=47°–48° C. to obtain 41.08 g of the expected product.

NMR Spectrum (CDCl3 250 MHz) 1.05 (d), 1.09 (d): CH3; 3.14 (m), 3.68 (m): —CH<; 3.24 (d): NH; 1.47 (s): tBu.

IR Spectrum (CHCl3): Absorptions at 3436 cm$^{-1}$ (NH); 1656 cm$^{-1}$ (C=N).

Step B: terbutyl (1R,cis) 2,2-dimethyl-3-[(Z) 2-[(1,1,1,3,3,3-hexafluoropropoxy)-carbonyl]-ethenyl]-cyclopropane-1-carboxylate.

0.055 g of sodium hydride (in suspension at 50% in oil) and 1 ml of toluene were mixed together under an inert gas atmosphere and then a solution of 0.162 g of hexafluoro isopropanol in 2 ml of toluene was added at +5°/+10° C. The mixture was stirred for 30 minutes at +10° C. and a solution of 0.184 g of terbutyl (1R,cis) 2,2-dimethyl-3-(1,3-dibromo-2-oxopropyl)-cyclopropane-1-carboxylate in 1.5 ml of toluene was added. The mixture was stirred for 2 hours at ambient temperature and was poured into 2N hydrochloric acid at +10° C. Extraction was carried out with ethyl acetate and the organic phase was washed with water, dried and evaporated to dryness. The residue was chromatographed on silica, eluting with a cyclohexane - ethyl acetate mixture (95-5) to obtain 0.135 g of the expected product melting at 95° C.

IR Spectrum (CHCl3): Absorption at 1742, 1710 cm$^{-1}$ (C=O) and 1622 cm$^{-1}$ (C=C).

NMR Spectrum (CDCl3 250 MHz): 1.28 (s), 1.32 (s): twinned CH3; 1.45 (s): H of tBu; 1.97–3.03: $H_1/H_3$ cis; 5.81 (seven): H of —CH(CF3)2; 5.99 (dd, J=11): H in position 2'; 7.00 (dd, J=11 and 10.5): H in position 1', Z isomer.

EXAMPLE 12

2,2,2-trichloroethyl (1R,cis) 2,2-dimethyl-3-[(Z) 2-[(1,1,1,3,3,3-hexafluoro-propoxy)-carbonyl]-ethenyl]-cyclopropane-1-carboxylate.

Step A: 2,2,2-trichloroethyl (1R,cis) 2,2-dimethyl-3-(1,3-dibromo-2-oxopropyl)-cyclopropane-1-carboxylate.

0.2 g of 2,2,2-trichloroethyl (1R,cis) 2,2-dimethyl-3-(2-oxopropyl)-cyclopropane-1-carboxylate, 3 ml of methylene chloride and 1 ml of chloroform were mixed together under an inert gas atmosphere and then 70 μl of bromine added at about +5° C. The mixture was stirred at ambient temperature for 3 hours and an ice-water mixture was added, followed by decanting and extracting with methylene chloride. The organic phase was dried and the solvent was evaporated. The residue was chromatographed in silica, eluting with a methylene chloride - cyclohexane mixture (7-3) to obtain 0.23 g of the expected product.

NMR Spectrum (CDCl3 250 MHz ppm): 1.22 (s), 1.31 (s) and 1.33 (s): twinned CH3; 1.94 to 2.10 (m): $H_1$ and $H_3$; 4.06 (d), 4.39 (d), 4.74 (d), 4.87 (d), 4.26 (s), 4.70 (s): 2 CH2—X; 5.24 (d) and 5.47 (d):

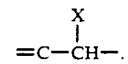

The starting ester was obtained as follows:

0.2 g of (1R,cis) 2,2-dimethyl-3-(2-oxopropyl)-cyclopropane-1-carboxylic acid, 4 ml of methylene chloride, 280 μl of pyridine and 0.267 g of dicyclohexylcarbodiimide were mixed together under an inert gas atmosphere and after 5 minutes, 135 μl of trichloroethanol and a few crystals of dimethylaminopyridine were added. The mixture was stirred for 20 hours at ambient temperature, followed by separation and evaporation to dryness. The residue was chromatographed on silica, eluting with a cyclohexane - ethyl acetate mixture (8-2) to obtain 0.316 g of the expected product.

IR Spectrum (CHCl3): Absence of acid and of OH. Absorption at 1732 and 1719 cm$^{-1}$ (C=O).

NMR Spectrum (CDCl3 250 MHz ppm): 1.18 (s), 1.26 (s): twinned CH3; 1.58 (m), 1.75 (d): $H_3$ and $H_1$ cis; 2.15 (s): CH3—C=O; 2.89 (m): =C—CH2—C; 4.70 (s): —CO2—CH2—.

Step B: 2,2,2-trichloroethyl (1R,cis) 2,2-dimethyl-3-[(Z) 2-[(1,1,1,3,3,3-hexafluoro-propoxy)-carbonyl]-ethenyl]-cyclopropane-1-carboxylate.

0.036 g of 50% sodium hydride and 1 ml of toluene were mixed together under an inert gas atmosphere and then a solution of 0.135 g of hexafluoroisopropanol in 0.5 ml of toluene was added at about 10° C. The mixture was stirred for 30 minutes at the same temperature and then a solution of 0.170 g of the product of Step A in 1 ml of toluene was added. The mixture was stirred for one hour and then the mixture was left at ambient temperature and stirred for one hour. 0.1N hydrochloric acid was then added at +10° C. until a pH of 1 was obtained and the mixture was stirred for 15 minutes. Extraction was carried out with ethyl acetate and the organic phase was dried and concentrated to dryness. The residue was chromatographed on silica, eluting with a methylene chloride - cyclohexane mixture (7-3) to obtain 0.1 g of expected product.

IR Spectrum (CHCl$_3$): Absorption at 1746 cm$^{-1}$ (C=O) and 1627 cm$^{-1}$ (C=C).

NMR Spectrum (CDCl$_3$ 250 MHz ppm): 1.35 (s): twinned CH$_3$; 2.19 (d) and 3.23 (m): H$_3$ and H$_1$ cis; 4.74 (A-B) —CO$_2$—CH$_2$—C; 5.8 (seven): F$_3$C—CH—CF$_3$; 6.04 (d, J=11.5): H in position 2'; 6.93 (dd): H in position 1'.

EXAMPLE 13

2,2,2-trichloroethyl (1R,cis) 2,2-dimethyl-3-[(Z) 2-(methoxycarbonyl)-ethenyl]-cyclopropane-1-carboxylate.

10 ml of methanol and 0.724 g of sodium methylate were mixed together under an inert gas atmosphere and 4 g of the product of Step A of Example 12 in 30 ml of methanol were added slowly at 0°,+5° C. The mixture was stirred for 16 hours at about +5° C. and was poured into a mixture of water and ice to which 15 ml of 2N hydrochloric acid had been added. After stirring for 15 minutes, extraction was carried out with methylene chloride. The organic phase was washed with water, dried and evaporated to dryness. The residue was chromatographed on silica, eluting with a methylene chloride - cyclohexane mixture (1-1) to obtain 0.879 g of the expected product.

NMR Spectrum (CDCl$_3$ 250 MHz ppm): 1.33 (s): twinned CH$_3$; 2.10 (d): H$_1$; 3.36 (m): H$_3$; 3.73 (s): CH$_3$—O—; 4.73 (A-B): —CO$_2$—CH$_2$—C; 5.93 (d, J=11.5): H in position 2'; 6.59 (dd): H in position 1'. Cis structure, delta Z.

EXAMPLE 14

2-chloroethyl (1R,cis) 2,2-dimethyl-3-[(Z) 2-[(1,1,1,3,3,3-hexafluoro-propoxy)-carbonyl]-ethenyl]-cyclopropane-1-carboxylate.

Step A: 2-chloroethyl (1R,cis) 2,2-dimethyl-3-(1,3-dibromo-2-oxopropyl)-cyclopropane-1-carboxylate.

0.235 g of 2-chloroethyl (1R,cis) 2,2-dimethyl-3-(2-oxopropyl)-cyclopropane-1-carboxylate and 5 ml of chloroform were mixed together under an inert gas atmosphere and then 100 μl of bromine were added slowly. The mixture was stirred at ambient temperature for 2 hours and then a water - ice mixture was added. The mixture was stirred for 15 minutes, followed by decanting and extracting with methylene chloride. The organic phase was dried and the solvent was evaporated. The residue was chromatographed on silica, eluting with a methylene chloride - hexane mixture (7-3) to obtain 0.067 g of the expected product.

NMR Spectrum (CDCl$_2$ 250 MHz ppm): 1.20 (s), 1.26 (s), 1.29 (s), 1.30 (s): twinned CH$_3$; 1.84 to 2.00 (m) H$_1$ and H$_3$; 3.64 (t), 3.72 (t); —CH$_2$Cl; 4.28 (t), 4.40 (m): —CO$_2$—CH$_2$—; 4.07 (d), 4.20 to 4.45 (m), 4.28 (m): C—CH$_2$—X; 5.23 (d) and 5.47 (d): =C—CHX—.

The starting ester was obtained as follows:

0.171 g of (1R,cis) 2,2-dimethyl-3-(2-oxopropyl)-cyclopropane-1-carboxylic acid and 0.7 ml of 1-bromo 2-chloroethane were mixed together under an inert gas atmosphere and then 145 μl of triethylamine were added slowly at 0°,+5° C. The mixture was stirred at ambient temperature and after a few hours, another 20 μl of triethylamine and 0.2 ml of bromochloroethane were added. The mixture was stirred at ambient temperature for 20 hours and then water was added, followed by decanting and extracting with methylene chloride. The organic phase was dried and evaporated to dryness. The residue was chromatographed on silica, eluting with a cyclohexane - ethyl acetate mixture (75-25) to obtain 0.172 g of the expected product.

NMR Spectrum (CDCl$_3$ 250 MHz ppm): 1.16 (s), 1.23 (s): twinned CH$_3$; 1.63 (d, J=8.5), 1.48 (m): H$_1$ and H$_3$ cis; 2.15 (s) —CH$_3$—CO—; 2.88 (m): —CH$_2$—CO—; 3.66 (t): —CH$_2$—Cl; 4.28 (m): CO$_2$—CH$_2$—.

IR Spectrum (CHCl$_3$): Absorption at 1720 cm$^{-1}$ (C=O), absence of acid.

Step B: 2-chloroethyl (1R,cis) 2,2-dimethyl-3-[(Z) 2-[(1,1,1,3,3,3-hexafluoro-propoxy)-carbonyl]-ethenyl]-cyclopropane-1-carboxylate.

3 ml of toluene and 0.11 g of 50% sodium hydride were mixed together under an inert gas atmosphere and then a solution of 0.5 g of 1,1,1,3,3,3-hexafluoroisopropanol in 1 ml of toluene was slowly added at +5°,+7° C. The mixture was stirred at the same temperature for 45 minutes and then a solution of 0.341 g of the product of Step A in 2 ml of toluene was added slowly. The mixture was stirred for 2 hours at +5°,+7° C. and for one hour at ambient temperature. The reaction medium was cooled to +10° C. and a small amount of acetic acid diluted by 50% was added, followed by decanting and extracting with ethyl acetate. The organic phase was dried and concentrated to dryness. The residue was chromatographed on silica, eluting with a methylene chloride - cyclohexane mixture (1-1) to obtain 0.11 g of the expected product.

NMR Spectrum (CDCl$_3$ 250 MHz ppm): 1.32 (s), 1.34 (s): twinned CH$_3$; 2.10 (d), 3.15 (m): H$_1$ and H$_3$ cis; 3.69 (t): —CH$_2$—Cl; 4.33 (t): CO$_2$—CH$_2$—; 5.81 (m): —CO$_2$—CH<; 6.01 (d, J=11): H in position 2'; 6.95 (dd): H in position 1'.

IR Spectrum (CHCl$_3$): Absorption at 1760, 1744 and 1726 cm$^{-1}$ (C=O complex), 1625 cm$^{-1}$ (C=C).

EXAMPLE 15

(S) α-cyano-3-phenoxybenzyl (1R,cis) 2,2-dimethyl-3-[(Z) 2-[(1,1,1,3,3,3-hexafluoropropoxy)-carbonyl)-ethenyl]-cyclopropane-1-carboxylate.

Using the procedure of Example 9, the ester of Step A of Example 7 was reacted to obtain after purification under the same conditions as Example 9, the expected product.

EXAMPLE 16

3,4,5,6-tetrahydrophthalimido-methyl (1R,cis) 2,2-dimethyl-3-[(Z)-2-[(1,1,1,3,3,3-hexafluoro-propoxy)-carbonyl]-ethyl]-cyclopropane-carboxylate.

Step A: 3,4,5,6-tetrahydrophthalimido-methyl (1R,cis) 2,2-dimethyl-3-(1,3-dibromo-2-oxopropyl)-cyclopropane-1-carboxylate.

0.8 g of 3,4,5,6-tetrahydrophthalimido-methyl (1R,cis) 2,2-dimethyl-3-(2-oxopropyl)-cyclopropane-1-carboxylate and 8 ml of tetrahydrofuran were mixed together under an inert gas atmosphere and then 1.72 g of pyridinium perbromide in the form of hydrobromide were added slowly. After 6 hours of stirring at +5° C., the precipitate was separated off and washed with tetrahydrofuran. Then, the filtrate was concentrated to dryness at 25° C. under reduced pressure, and the residue was chromatographed on silica, eluting with methylene chloride to obtain 0.31 g of the expected product.

NMR Spectrum (CDCl$_3$ 250 MHz ppm): 1.22 (s), 1.19 (s), 1.25 (s) and 1.30 (s): twinned CH$_3$; 1.76 (d) and 1.34 (m): H$_1$ and H$_3$; 1.78 (m): CH$_2$ in beta position and 2.38 (m) CH$_2$ in α position in the tetrahydro-phthalimide ring; 4.07 (d), 4.36 (d) and 4.28 (AB system): —COCH$_2$Br; 5.22 (d), 5.55 (d) and 5.57 (AB system): —CO$_2$CH$_2$—; 5.40 (d) and 5.42 (d): —COCHBr—.

The starting ester was obtained as follows:

1 g of 2,2-dimethyl-3-(2-oxopropyl)-cyclopropane-1-carboxylic acid, 8 ml of methylene chloride, 1.395 ml of pyridine and 1.29 g of dicyclohexylcarbodiimide were mixed together under an inert gas atmosphere and then a solution of 1.1 g of 3,4,5,6-tetrahydrophthalimido-methyl alcohol in 5 ml of methylene chloride was introduced at +5° C. A few milligrams of 4-dimethylaminopyridine were added and the mixture was stirred for 18 hours while allowing the temperature to rise. After filtration, the filtrate was concentrated to dryness under reduced pressure at 30° C. and the residue was chromatographed on silica, eluting with a cyclohexane -ethyl acetate mixture (7-3) to obtain 1.336 g of the expected product.

NMR Spectrum (CDCl$_3$ 250 MHz ppm): 1.22 (s), 1.19 (s), 1.25 (s) and 1.30 (s): twinned CH$_3$; 1.76 (d) and 1.34 (m): H$_1$ and H$_3$; 1.78 (m) and 2.38 (m): CH$_2$ in beta position and CH$_2$ in α position in the tetrahydrophthalimide ring; 4.07 (d), 4.36 (d) and 4.28 (AB system): —COCH$_2$Br; 5.22 (d), 5.55 (d) and 5.57 (AB system): —CO$_2$CH$_3$—; 5.40 (d) and 5.42 (d): —COCHBr—.

Step B: 3,4,5,6-tetrahydrophthalimido-methyl (1R,cis) 2,2-dimethyl 3-[(Z)-2-[(1,1,1,3,3,3-hexafluoro propoxy)-carbonyl]-ethenyl]- cyclopropane-carboxylate.

1 ml of toluene and 20 mg of sodium hydride at 50% in oil were mixed together under an inert gas atmosphere and the mixture was cooled to +5+, +10° C. A solution of 67 mg of hexafluoroisopropanol in 0.5 ml of toluene was added slowly and after stirring for 30 minutes at 10° C., a solution of 0.1 g of the product of Step A in 1 ml of toluene was added. The mixture was stirred while allowing the temperature to rise and after 2 hours, the mixture was poured into a 2N hydrochloric acid - ice mixture. The mixture was stirred for 5 minutes, followed by extraction with ethyl acetate. The organic phase was washed with water, dried and concentrated to dryness at 30° C. under reduced pressure. The residue was chromatographed on silica, eluting with methylene chloride to obtain 0.04 g of the expected product.

NMR Spectrum (CDCl$_3$ 250 MHz ppm): 1.28 (s) and 1.32 (s): twinned CH$_3$; 1.98 (d, J=8.5) and 3.13 (m): H$_1$ and H$_3$ (cis); 1.78 (m) and 2 38 (m): CH$_2$ in beta position and CH$_2$ in α position in the tetrahydrophthalimide ring; 5.52 (AB system): —CO$_2$—CH$_2$—N; 6.01 (d, J=11.5): H in position 1'; 6.94 (dd, J=10.5 and 11.5): H in position 2'; 5.80 (m): —CO$_2$—CH—(CF$_3$)$_2$.

EXAMPLE 17 pentafluorobenzyl (1R,cis) 2,2-dimethyl-3-[(Z) 2-(methoxycarbonyl)-ethenyl]-cyclopropane-1-carboxylate.

Step A: pentafluorobenzyl (1R,cis) 2,2-dimethyl-3-(1,3-dibromo-2-oxypropyl)-cyclopropane-1-carboxylate.

1.2 of pentafluorobenzyl (1R,cis) 2,2-dimethyl-3-(2-oxopropyl)-cyclopropane-1-carboxylate and 12 ml of tetrahydrofuran were mixed together under an inert gas atmosphere and 2.45 g of pyridinium hydrobromide perbromide were added slowly at +5° C. Then, the mixture was stirred at +5° C. for 7 hours and after filtration, the filtrate was concentrated to dryness under reduced pressure at 25° C. The residue was chromatographed on silica, eluting with a methylene chloride - hexane mixture (7-3) to obtain 1.08 g of the expected product.

NMR Spectrum (CDCl$_3$ 250 MHz ppm): 1.20 (s), 1.24 (s), 1.26 (s) and 1.30 (s): twinned CH$_3$; 1.73 (d) and 1.96 (m): H$_1$ and H$_3$; 4.07 (d), 4.37 (d) and 4.26 (s): CO$_2$—CH$_2$; 5.15 and 5.22: —COCH$_2$Br—; 5.20 (d) and 5.41 (d): —COCHBr—.

The starting ester was obtained as follows:

0.165 g of (1R,cis) 2,2-dimethyl-3-(2-oxopropyl)-cyclopropane-1-carboxylic acid, 2 ml of methylene chloride, 230 μl of pyridine and 0.213 g of dicyclohexylcarbodiimide were mixed together under an inert gas atmosphere and then a mixture of 0.2 g of pentafluorobenzyl alcohol, 1 ml of methylene chloride and a few milligrams of 4-dimethylaminopyridine was added. The temperature was allowed to rise and the mixture was stirred for 12 hours. After filtration, the filtrate was rinsed with methylene chloride and concentrated to dryness. The residue was purified by chromatography on silica, eluting with a cyclohexane - ethyl acetate mixture (80-20) to obtain 0.25 g of the expected product.

NMR Spectrum (CDCl$_3$ 250 MHz ppm): 1.16 (s) and 1.20 (s): twinned CH$_3$; 1.48 (m) and 1.68 (d): H of the cyclopropyl (cis); 2.14 (s): —CO—CH$_3$; 2.88 (m): —COCH$_2$—; 5.15 (AB system): —CO$_2$CH$_2$—.

Step B: pentafluorobenzyl (1R,cis) 2,2-dimethyl-3-[(Z) 2-(methoxycarbonyl)-ethenyl]-cyclopropane-1-carboxylate.

0.022 g of sodium methylate and 0.3 ml of methanol were mixed together under an inert gas atmosphere and then a solution of 0.1 g of the product of Step A in 1 ml of methanol was added slowly at 0°,+5° C. The mixture was stirred for 2 hours and then poured into a mixture of water and ice and 0.75 ml of 2N hydrochloric acid. The mixture was stirred for 15 minutes, followed by extraction with methylene chloride. The organic phase was washed with water and dried, then concentrated to dryness at 30° C. under reduced pressure. The residue was chromatographed on silica, eluting with a methylene chloride - hexane mixture (7-3) to obtain 0.031 g of the expected product.

NMR Spectrum (CDCl$_2$ 250 MHz ppm): 1.28 (s) and 1.31 (s): twinned CH$_3$; 1.93 (d, J=8.5) and 3.28 (m): H$_1$ and H$_3$ cis; 3.72 (s): —COOCH$_3$; 5.18 (s): —CO$_2$—CH$_2$; 5.91 (d, J=12): H in position 1'; 6.60 (dd, J=12 and 10) H in position 2'.

EXAMPLE 18 pentafluorobenzyl (1R,cis) 2,2-dimethyl-3-[(Z) 2-[(1,1,1,3,3,3-hexafluoro)-propoxycarbonyl)-ethenyl]-cyclopropane-1-carboxylate.

0.03 g of sodium hydride at 50% in oil and 1 ml of toluene were mixed together under an inert gas atmosphere and a solution of 0.099 g of hexafluoro-isopropanol in 1 ml of toluene was added slowly at +5°,+10° C. The mixture was stirred for 30 minutes and then a solution of 0.15 g of the product of Step A of Example 17 in 1 ml of toluene was added. The mixture was stirred for 2 hours while allowing the temperature to rise and then was poured into a mixture of 2N hydrochloric acid and ice. Extraction was carried out with ethyl acetate and the organic phase was washed with water and dried, then concentrated to dryness under reduced pressure. The residue was chromatographed on silica to obtain 0.102 g of the expected product.

NMR Spectrum (CDCl$_3$ 250 MHz ppm): 1.30 (s) and 1.33 (s): twinned CH$_3$; 2.03 (d, J=8.5) and 3.15 (m): H$_1$ and H$_3$ cis; 5.20 (AB system): —CO$_2$—CH$_2$—; 5.80 —CO$_2$—CH; 6.03 (d, J=11.5): H in position 1'; 6.03 (m): H in position 2' delta Z.

EXAMPLE 19 terbutyl (1R,cis) 2,2-dimethyl-3-[(Z) 2-(methoxycarbonyl)-ethenyl]-cyclopropane-1-carboxylate.

0.02 g of sodium and 0.5 ml of toluene were mixed together under an inert gas atmosphere and then 0.2 ml of methanol was added slowly at about 5° C. The mixture was stirred for 30 minutes at ambient temperature and then the mixture was cooled to 5° C. A solution of 0.0768 g of the product of Step A of Example 11 in 1 ml of toluene was added and the mixture was stirred for 3 hours while allowing the temperature to rise, followed by acidification to pH 3-4 by adding 2N hydrochloric acid. 5 ml of toluene were added, followed by decanting and the organic phase was washed with water, dried and the solvent was evaporated. The residue was chromatographed on silica, eluting with a cyclohexane - isopropyl ether mixture (8-2) to obtain 0.03 g of the expected product.

NMR Spectrum (CDCl$_3$ 250 MHz ppm): 1.26 (s), 1.29 (s): twinned CH$_3$; 1.80 (d, J=8.5), 3.14 (dd): H$_1$ and H$_3$ cis; 1.44 (s): CO$_2$tBu; 3.71 (s): CO$_2$CH$_3$; 5.89 (d, J=11.5), 6.65 (dd, J=11.5 and 10.5): H in α and beta positions of CO$_2$CH$_3$, Z structure.

Various modifications of the process of the invention may be made without departing from the spirit or scope thereof and it is to be understood that the invention is intended to be limited only as defined in the appended claims.

What is claimed is:

1. A process for the preparation of a compound of the formula

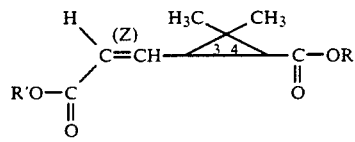

wherein R is either a remainder of a cleavable ester or a remainder of an ester known for pyrethrinoids selected from the group consisting of:

a) benzyl optionally substituted on the aromatic vertices by at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy and halogen;

b)

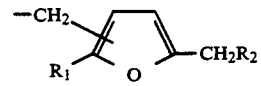

in which R$_1$ is hydrogen or methyl and R$_2$ is a monocyclic aryl or —C≡CH;

c)

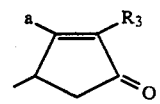

in which a hydrogen or methyl and R$_3$ is aliphatic of 2 to 6 carbon atoms and having at least one carbon-carbon unsaturation;

d)

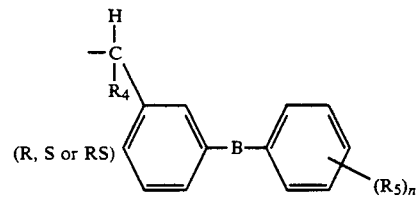

in which B is oxygen or sulfur or

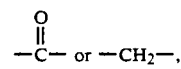

R$_4$ is selected from the group consisting of hydrogen, chlorine, bromine, iodine, —C≡N, methyl, —CONH$_2$. —CSNH$_2$ and —C≡CH, R$_5$ is halogen or methyl and n is 0, 1 or 2;

e)

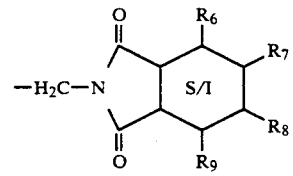

in which R$_6$, R$_7$, R$_8$ and R$_9$ are hydrogen, chlorine or methyl and in which S/I symbolizes an aromatic ring or a dihydro, tetrahydro or hexahydro ring, f) (succimido or maleimido) methylene;

g)

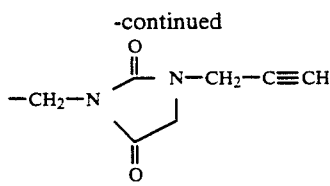

h)

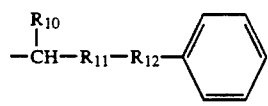

in which $R_{10}$ is hydrogen or CN, $R_{12}$ is —$CH_2$ or oxygen, $R_{11}$ is thiazolyl or thiadiazolyl whose bond with

can be found in any one of the available positions, $R_{12}$ being linked to $R_{11}$ by the carbon atom contained between the sulfur and the nitrogen;

i)

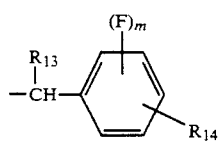

in which $R_{13}$ is hydrogen or —CN or —C≡CH, $R_{14}$ is trifluoromethyl or alkyl, alkenyl or alkynyl of up to 6 carbon atoms and m is a number of 1, 2, 3 or 4;

j)

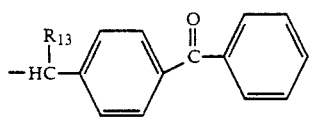

in which $R_{13}$ is defined as above;

k)

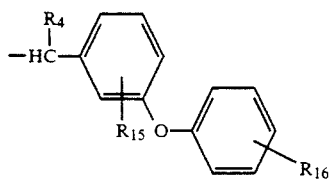

in which $R_4$ is defined as above, $R_{15}$ is fluorine, chlorine or bromine and $R_{16}$ is hydrogen, fluorine, chlorine or bromine;

l)

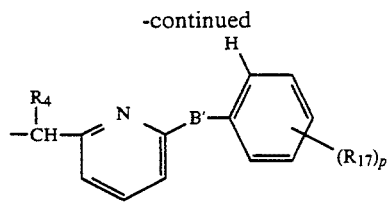

in which $R_4$ is defined as above, each of $R_{17}$ is independently selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, trifluoromethyl, 3,4-methylenedioxy, chloro, fluoro or bromo, p is 0, 1 or 2 and B' is oxygen or sulfur;

m)

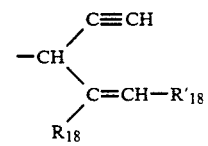

in which $R_{18}$ is fluorine or methyl and $R'_{18}$ is methyl, ethyl or propargyl;

n)

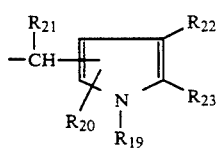

in which $R_{21}$ is hydrogen —C≡N, —C≡CH, —$CF_3$ or alkyl of 1 to 3 carbon atoms, $R_{20}$, $R_{22}$ and $R_{23}$ individually are selected from the group consisting of hydrogen, halogen, alkyl of 1 to 18 carbon atoms, aryl of up to 14 carbon atoms, aralkyl of up to 18 carbon atoms, cyano, —$CF_3$, —$CO_2$-alkyl of up to 8 carbon atoms, $NO_2$, alkoxy of up to 8 carbon atoms,

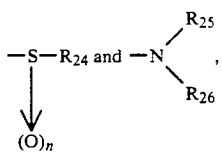

n is 0, 1 and 2 and $R_{24}$, $R_{25}$ and $R_{26}$ are alkyl of 1 to 8 carbon atoms, $R_{22}$ and $R_{23}$ being able to form a saturated or unsaturated carbonaceous homocycle of up to 8 carbon atoms and $R_{19}$ is:
a) either

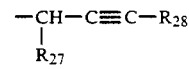

in which $R_{27}$ and $R_{28}$ are individually hydrogen, halogen, alkyl of 1 to 8 carbon atoms or aryl of up to 14 carbon atoms;
b) or

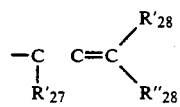

in which R'$_{27}$, R'$_{28}$ and R"$_{28}$ are individually one of the values for R$_{27}$ and R$_{28}$, the dotted lines being an optional second bond;

c) or

in which R$_{29}$ can have the values indicated for R$_{22}$ and R$_{23}$ with the exception of halogen, cyano, —NO$_2$,

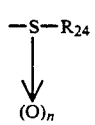

in which n is 1 or 2 and

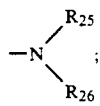

d) or

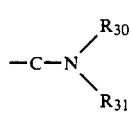

in which R$_{30}$ and R$_{31}$ are individually hydrogen, alkyl of 1 to 18 carbon atoms, aryl of up to 14 carbon atoms, aralkyl of up to 18 carbon atoms, —CF$_3$, —CO$_2$-alkyl of up to 8 carbon atoms or alkoxy of up to 8 carbon atoms, o)

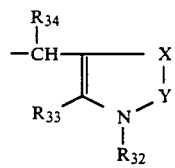

in which X is sulfur or oxygen, Y is >C=O, >C=S or —CH$_2$, R$_{32}$ is selected from the group consisting of saturated or unsaturated, alkyl or cycloalkyl of up to 8 carbon atoms optionally substituted by at least one halogen and aryl of up to 14 carbon atoms, R$_{33}$ is selected from the group consisting of hydrogen, saturated or unsaturated alkyl or cycloalkyl of up to 8 carbon atoms optionally substituted by at least one halogen, aryl of up to 14 carbon atoms, —CF$_3$, —NO$_2$ —C≡N, halogen, alkoxy of up to 8 carbon atoms and —CO$_2$-alkyl of up to 8 carbon atoms, R$_{34}$ is hydrogen, alkyl of 1 to 3 carbon atoms or —C≡CH;

p)

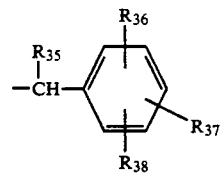

in which R$_{35}$ is selected from the group consisting of hydrogen, alkyl of 1 to 3 carbon atoms, —C≡N, —C≡CH and —CF$_3$, R$_{36}$ and R$_{38}$ are individually selected from the group consisting of hydrogen, alkyl of 1 to 3 carbon atoms optionally substituted by at least one halogen, alkenyl of 2 to 4 carbon atoms and halogen and R$_{37}$ is phenyl optionally substituted by at least one alkyl of 1 to 3 carbon atoms or by at least one halogen, R' is selected from the group consisting of hydrogen, saturated or unsaturated alkyl of 1 to 18 carbon atoms optionally substituted by at least one identical or different functional groups, or R' is cycloaliphatic of 3 to 7 carbon atoms substituted by at least one identical or different functional group, or R' is aryl of 6 to 14 carbon atoms optionally substituted by at least one identical or different functional group, or R' is heterocyclic optionally substituted by at least one identical or different functional group, in the form of mixtures of isomers or separate isomers at the level of the cyclopropane ring comprises reacting an ester of the formula

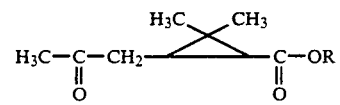

in which R is defined as above with a halogenation agent to obtain a compound of the formula

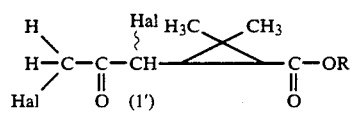

in which R is defined as above, and Hal is halogen in the form of a mixture of isomers at the level of the carbon atom in position 1' and treating the latter with a basic agent in the presence of a compound of the formula R'—OH, in which R' is defined as above to obtain the corresponding compound of formula I.

2. The process of claim 1 wherein the halogenation agent is a chlorination or bromination agent.

3. The process of claim 2 wherein the halogenation agent is selected from the group consisting of bromine, chlorine, N-bromo and N-chloro succinimide and acetamide, pyridinium perbromide and perchloride and pyridinium hydrobromide and hydrochloride perbromide and perchloride.

4. The process of claim 1 wherein about 2 equivalents of the halogenation agent are used.

5. The process of claim 1 wherein the basic agent is selected from the group consisting of hydrides, alcoholates, amides, alkali metal and alkaline-earth metal carbonates and tertiary amines.

6. The process of claim 1 wherein the action of the basic agent in the presence of a compound of formula R'—OH is carried out in an appropriate cosolvent.

7. The process of claim 1 wherein R is a cleavable ester remainder in acid or neutral medium selected from the group consisting of alkyl of 1 to 18 carbon atoms, alkyl of 1 to 18 carbon atoms substituted by at least one halogen, alkyl of 1 to 4 carbon atoms substituted by a silyl and alkyl of 1 to 4 carbon atoms substituted by O-alkyl, O-aryl or O-aralkyl, alkyl of 1 to 4 carbon atoms and aryl of 6 to 14 carbon atoms.

8. The process of claim 7 wherein R is a cleavable ester remainder in acid or neutral medium selected from the group consisting of alkyl of 1 to 4 carbon atoms, alkyl of 1 to 4 carbon atoms substituted by at least one chlorine or bromine, alkyl of 1 to 4 carbon atoms substituted by an alkylsilyl, alkyl of 1 to 4 carbon atoms substituted by O-alkyl, O-aryl or O-aralkyl, as defined in claim 7.

9. The process of claim 7 wherein R is alkyl of 1 to 4 carbon atoms, or methyl or ethyl substituted by at least one chlorine or bromine.

10. The process of claim 1 wherein R is an ester remainder selected from the group consisting of:

a) benzyl substituted by at least one halogen, b)

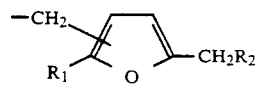

in which $R_1$ and $R_2$ are defined as previously, c)

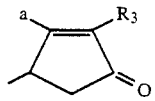

in which a and $R_3$ are defined as previously, d)

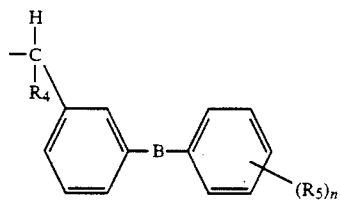

in which $R_4$, $R_5$ and n are defined as previously, e)

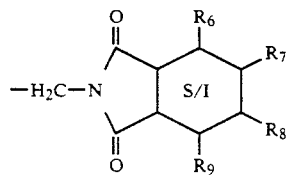

in which $R_6$, $R_7$, $R_8$, $R_9$ and S/I are defined as previously, f)

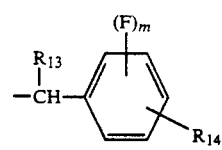

in which $R_{13}$, $R_{14}$ and m are defined as previously, g)

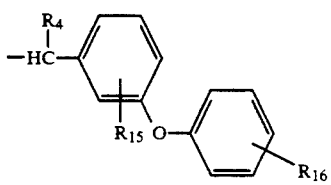

in which $R_4$, $R_{15}$ and $R_{16}$ are defined as previously, h)

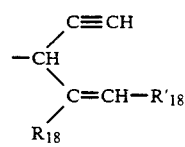

in which $R_{18}$ and $R'_{18}$ are defined as previously and i)

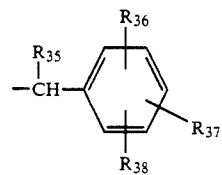

in which $R_{35}$, $R_{36}$, $R_{37}$ and $R_{38}$ are defined as previously.

11. The process of claim 10 wherein R is an ester remainder selected from the group consisting of:

a) benzyl substituted by 1 to 5 fluorine b)

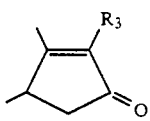

in which $R_3$ is —$CH_2$—CH—$CH_2$ or —$CH_2$—C≡CH, c)

-continued

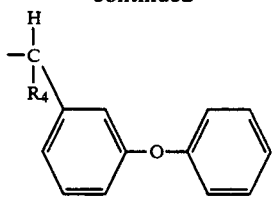

in which R₄ is defined as previously, d)

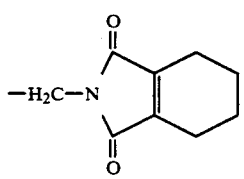

e)

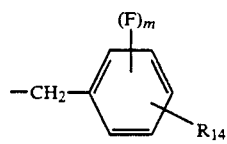

in which R₁₄ and m are defined as previously, f)

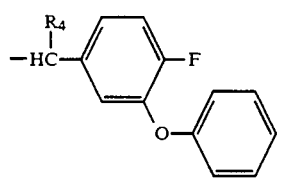

in which R₄ is defined as previously, g)

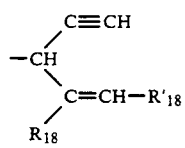

in which R₁₈ and R'₁₈ are defined as previously and h)

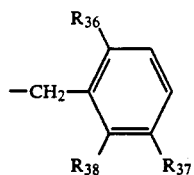

in which R₃₆ is hydrogen, fluorine or chlorine, R₃₇ is a phenyl or 3-fluorophenyl and R₃₈ is hydrogen, fluorine or chlorine, or methyl.

12. The process of claim 1 wherein a compound of formula R'—OH is used at the start in which R' is selected from the group consisting of hydrogen, alkyl or cyclo alkyl of up to 8 carbon atoms, alkyl of 1 to 8 carbon atoms substituted by at least one halogen, $(CH_2)_m-O-(CH_2)_n-CH_3$ in which m is an integer from 1 to 8 and n is an integer from 0 to 8.

13. The process of claim 1 wherein a compound of formula II of (1R,cis) structure in which R is a remainder of (R,S) or (S) α-cyano-3-phenoxybenzyl alcohol or a remainder of (R,S) or (S) α-cyano-4-fluoro 3-phenoxybenzyl alcohol and a compound of formula R'—OH in which R' is methyl, ethyl, terbutyl or 1,1,1,3,3,3-hexafluoropropyl are used at the start.

14. A compound of the formula

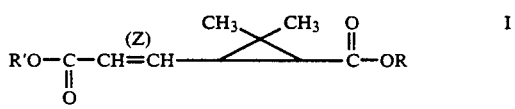

wherein R' is defined as in claim 1 and R is selected from the group consisting of bromomethyl, chloromethyl and ethyl substituted with 1 to 3 bromine or chlorine.

15. A compound in isomeric form or mixtures thereof of the formulae

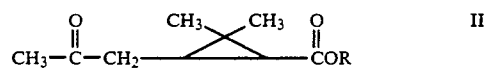

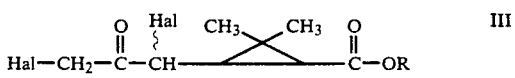

(I')

wherein R is defined as in claim 1 except in formula III R is not —CH₃, ethyl, 3-phenoxybenzyl or α-cyano-3-phenoxybenzyl and Hal is halogen.

* * * * *